(12) United States Patent
Boyle et al.

(10) Patent No.: US 7,018,393 B1
(45) Date of Patent: Mar. 28, 2006

(54) SHEATHLESS EMBOLIC PROTECTION SYSTEM

(75) Inventors: William J. Boyle, Fallbrook, CA (US); Richard S. Stack, Chapel Hill, NC (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 253 days.

(21) Appl. No.: 09/945,152

(22) Filed: Aug. 31, 2001

Related U.S. Application Data (63) Continuation-in-part of application No. 09/740,560, filed on Dec. 19, 2000, now Pat. No. 6,506,203.

(51) Int. Cl.
*A61M 29/00* (2006.01)

(52) U.S. Cl. .................................... 606/200

(58) Field of Classification Search ............... 606/200, 606/113, 127
See application file for complete search history.

(56) References Cited

U.S. PATENT DOCUMENTS

| | | |
|---|---|---|
| 4,723,549 A | 2/1988 | Wholey et al. |
| 4,997,435 A | 3/1991 | Demeter |
| 5,100,425 A | 3/1992 | Fischell et al. |
| 5,158,548 A | 10/1992 | Lau et al. |
| 5,437,632 A | 8/1995 | Engelson |
| 5,649,953 A * | 7/1997 | Lefebvre ............... 606/200 |
| 5,814,064 A | 9/1998 | Daniel et al. |
| 5,827,324 A | 10/1998 | Cassell et al. |
| 5,846,251 A | 12/1998 | Hart |
| 5,911,734 A | 6/1999 | Tsugita et al. |
| 5,980,555 A | 11/1999 | Barbut et al. |
| 5,989,281 A | 11/1999 | Barbut et al. |
| 6,187,025 B1 * | 2/2001 | Machek ................ 606/200 |
| 6,511,497 B1 * | 1/2003 | Braun et al. ........... 606/200 |

* cited by examiner

Primary Examiner—(Jackie) Tan-Uyen T. Ho
(74) Attorney, Agent, or Firm—Fulwider Patton LLP

(57) ABSTRACT

A system for enabling the insertion and removal of an embolic protection device, for capturing and retaining embolic debris which may be created during the performance of a therapeutic interventional procedure in a stenosed or occluded region of a blood vessel. The system, in an embodiment thereof, enables the device to be compressed for insertion thereof through a patient's vasculature so as to cross the stenosis in a low profile, and to enable release of compression thereof for expansion and deployment of the device at a location distal to the interventional procedure site.

35 Claims, 5 Drawing Sheets

SHEATHLESS EMBOLIC PROTECTION SYSTEM

RELATED APPLICATIONS

This application is a continuation-in-part of application Ser. No. 09/740,560 filed on Dec. 19, 2000 U.S. Pat. No. 6,506,203.

BACKGROUND OF THE INVENTION

The present invention relates generally to improvements in embolic protection systems and methods. In particular, it relates to an improved system and method for enabling an embolic protection device to be efficiently and conveniently compressed and retained in compressed condition so as to cross a stenosis in a low 110 profile and be delivered through the patient's vasculature to a location distal to the site of an interventional procedure, without a sheath extending about the filter device. The system also enables the device to be effectively released from compression thereof at the location distal to the interventional procedure site, for enabling expansion and deployment of the filter device for capturing embolic material.

The systems and methods of the present invention are particularly useful when performing balloon angioplasty, stenting procedures, laser angioplasty or atherectomy in critical vessels, such as the carotid, renal, and saphenous vein graft arteries, where the release of embolic debris into the bloodstream could possibly occlude the flow of oxygenated blood to the brain or other vital organs which can cause devastating consequences to the patient.

A variety of non-surgical interventional procedures have been developed over the years for opening stenosed or occluded blood vessels in a patient caused by the build up of plaque or other substances on the walls of the blood vessel. Such procedures usually involve the percutaneous introduction of the interventional device into the lumen of the artery, usually through a catheter. One widely known and medically accepted procedure is balloon angioplasty in which an inflatable balloon is introduced within the stenosed region of the blood vessel to dilate the occluded vessel. The balloon catheter is initially inserted into the patient's arterial system and is advanced and manipulated into the area of stenosis in the artery. The balloon is inflated to compress the plaque and press the vessel wall radially outward to increase the diameter of the blood vessel.

Another procedure is laser angioplasty which utilizes a laser to ablate the stenosis by super heating and vaporizing the deposited plaque. Atherectomy is yet another method of treating a stenosed blood vessel in which a cutting blade is rotated to shave the deposited plaque from the arterial wall. A vacuum catheter may be used to capture the shaved plaque or thrombus from the blood stream during this procedure.

In another widely practiced procedure, the stenosis can be treated by placing a device known as a stent into the stenosed region to hold open and sometimes expand the segment of the blood vessel or other arterial lumen. Stents are particularly useful in the treatment or repair of blood vessels after a stenosis has been compressed by percutaneous transluminal coronary angioplasty (PTCA), percutaneous transluminal angioplasty (PTA) or removal by atherectomy or other means. Stents are usually delivered in a compressed condition to the target site, and then are deployed at the target location into an expanded condition to support the vessel and help maintain it in an open position.

In the past, stents typically have fallen into two general categories of construction. The first type of stent is expandable upon application of a controlled force, often through the inflation of the balloon portion of a dilatation catheter which, upon inflation of the balloon or other expansion means, expands the compressed stent to a larger diameter to be left in place within the artery at the target site. The second type of stent is a self-expanding stent formed from, for example, shape memory metals or super-elastic nickel-titanum (NiTi) alloys, which will automatically expand from a compressed state when the stent is advanced out of the distal end of the delivery catheter into the body lumen. Such stents manufactured from self-expandable materials allow for phase transformations of the material to occur, contributing to the expansion and contraction of the stent.

The above non-surgical interventional procedures, when successful, avoid the necessity of major surgical operations. However, there is one common problem associated with all of these non-surgical procedures, namely, the potential release of embolic debris into the bloodstream which can occlude distal vasculature and cause significant health problems to the patient. For example, during deployment of a stent, it is possible that the metal struts of the stent can cut into the stenosis and shear off pieces of plaque which become embolic debris that can travel downstream and lodge somewhere in the patient's vascular system. Pieces of plaque material can sometimes dislodge from the stenosis during a balloon angioplasty procedure and become released into the bloodstream. Additionally, while complete vaporization of plaque is the intended goal during a laser angioplasty procedure, particles are not always fully vaporized and may enter the bloodstream.

When any of the above-described procedures are performed for example in the carotid arteries, the release of emboli into the circulatory system can be extremely dangerous to the patient. Debris that is carried by the bloodstream to distal vessels of the brain may cause these cerebral vessels to occlude, resulting in a stroke, and in some cases, death. Therefore, although carotid percutaneous transluminal angioplasty has been performed in the past, the number of procedures performed has been limited due to the justifiable fear of causing an embolic stroke should embolic debris enter the bloodstream and block vital downstream blood passages.

Medical devices have been developed to attempt to deal with the problem created when debris or fragments enter the circulatory system following treatment utilizing any one of the above-identified procedures. One approach which has been attempted is the cutting of any debris into minute sizes which pose little chance of becoming occluded in major vessels within the patient's vasculature. However, it is often difficult to control the size of the fragments which are formed, and the potential risk of vessel occlusion still exists, making such procedures in the carotid arteries a high-risk proposition.

Other techniques which have been developed to address the problem of removing embolic debris include the use of catheters with a vacuum source which provides temporary suction to remove embolic debris from the bloodstream. However, as mentioned above, there have been complications with such systems since the vacuum catheter may not always remove all of the embolic material from the bloodstream, and a powerful suction could cause problems to the patient's vasculature.

Further techniques which have had some limited success include the placement of an embolic protection device such as a filter or trap downstream from the treatment site to capture embolic debris before it reaches the smaller blood vessels downstream. Such embolic protection devices enable the filtering of embolic debris which may be released into the bloodstream during the treatment to the vessel, and yet allow a sufficient amount of oxygenated blood to flow past the device to supply vital organs downstream from the treatment site.

However, there have been problems associated with filtering systems, particularly during the insertion, expansion, deployment, and removal of the filter within the blood vessel. The filter needs to cross the stenosis in as small a profile as possible so as to clear the stenosis and prevent damage thereto. Previous designs have employed an outer catheter called a "sheath" to keep these filters constrained prior to delivery beyond the stenosis. This outer catheter necessarily increases the profile of the device which could in and of itself create embolic complications as this high profile device is forced through the stenosis. After crossing the stenosis and being positioned distal to the interventional procedure site, the filter needs to be deployed, and after the interventional procedure has been performed, the filter needs to be removed with the captured embolic material therein, in an efficient and effective manner.

Therefore, the present invention provides improved systems and methods for treating stenosis in blood vessels which reduces the profile and improves the stenosis crossing characteristics of a filter, for crossing the stenosis to a position distal to the interventional procedure site for deployment of the filter. It also enables effective filter deployment at the position distal to the interventional procedure site, and removal from the position distal to the interventional procedure site, for capturing embolic debris in the bloodstream that can cause blockage in vessels at downstream locations. The improved systems and methods of the present invention further enable filtering of embolic debris which may be released into the bloodstream during the treatment to the vessel, and allow a sufficient amount of oxygenated blood to flow past the filtering device to supply vital organs downstream from the treatment site. Moreover, the systems and methods are relatively easy for a physician to use, while enabling the effective delivery and recover of a filtering system capable of removing embolic debris released into the bloodstream. The inventions disclosed herein satisfy these and other needs.

SUMMARY OF THE INVENTION

The present invention, in general, provides a system and method for enabling the insertion and removal of a filtering system for capturing and retaining embolic debris from a blood vessel. The embolic debris may be created during the performance of a therapeutic interventional procedure, such as a balloon angioplasty or stenting procedure. The filtering system prevents the embolic debris from lodging and blocking blood vessels downstream from the interventional site. The present invention is particularly useful for enabling an interventional procedure to be performed in vital arteries, such as the carotid arteries, in which critical downstream blood vessels can become blocked with embolic debris, including the main blood vessels leading to the brain or other vital organs. As a result, the present invention provides the physician with a higher degree of confidence in the efficient operation of a filtering system for the collection and removal of embolic debris from the blood vessel when performing high-risk interventional procedures.

The present invention enables a filtering system to be deployed in the blood vessel at a location distal to the area of treatment in the interventional procedure site. It also enables the blood to pass therethrough to enable blood to flow past the filter. It further enables the blood to be filtered to capture and retain any embolic debris which may be created during the interventional procedure.

More particularly, for example, in an embodiment of the present invention, a system is provided for enabling the capture of embolic material which may be released into a blood vessel during a therapeutic interventional procedure at a site of a stenosis. The present invention also enables the system to expand against the inner surface of a wall of a blood vessel so as to efficiently seal off the inner surface thereof, for enabling the capture of embolic material which may be released into the blood vessel during the therapeutic interventional procedure. Further, the system enables navigation thereof through a patient's blood vessel, including tortuous vasculature, to a position distal to an interventional procedure site, for deployment of the embolic protection device.

The system includes a guide wire, including a distal end, which is positionable within the blood vessel so as to extend to a position distal to an interventional procedure site. The system also includes a filter device, which is positionable and able to be deployed at a location in the patient's vasculature distal to the interventional procedure site, and to capture embolic material which may be released into the blood in the blood vessel during the interventional procedure. The system further includes a compressing element, for compressing the filter device so as to enable the filter device to be inserted over the guide wire, to the position distal to the interventional procedure site, in a low profile for crossing the stenosis, and without a sheath extending about the filter device. The filter device also enables the release of the compressing element, so as to enable expansion of the filter device for deployment thereof.

The above objects and advantages of the present invention, as well as others, are described in greater detail in the following description, when taken in conjunction with the accompanying drawings of illustrative embodiments.

DETAILED DESCRIPTION OF THE PREFERRED EMBODIMENTS

The present invention is directed to an improved system and method for enabling the capture of embolic material which may be released into the blood vessel during a therapeutic interventional procedure, in an efficient and effective manner. The invention enables a filter device to be compressed, for efficient insertion thereof through the patient's vasculature so as to cross a stenosis in a low profile at the site of the interventional procedure, without a sheath extending about the filter device. The present invention is further directed to effectively enabling the release of compression thereof, for expansion and deployment of the filter device at a location distal to the interventional procedure site.

The embodiments of the improved system and method are illustrated and described herein by way of example only and not by way of limitation. While the present invention is described as applied to the carotid arteries of the patient, those skilled in the art will appreciate that it can also be used in other body lumens as well, such as the coronary arteries, renal arteries, saphenous vein grafts and other peripheral arteries. Additionally, the present invention can be utilized when performing any one of a number of interventional procedures, such as stenting, balloon angioplasty, laser angioplasty or atherectomy.

In the drawings, wherein like reference numerals denote like or corresponding parts throughout the drawing figures, and particularly in the embodiments in accordance with the invention as shown in FIGS. 1–10, for example, a system 10 is provided for enabling an interventional procedure to be performed in a blood vessel 12 at an area of treatment 14. The system 10 is atraumatic, to inhibit injury to the patient. It includes a guide wire 16 which enables the system 10 to be positioned distal to the area of treatment 14. The system 10 is placed within the carotid artery 18 or other blood vessel of the patient, and is guided into position by the guide wire 16. The guide wire 16 includes a tip coil 20 at a distal end 22 thereof. The tip coil includes a proximal end 24. The tip coil 20 is attached at the proximal end thereof to the guide wire 16 for example by solder. The carotid artery 18 has the area of treatment 14 therein, which comprises the interventional procedure site, wherein atherosclerotic plaque 26 has built up against the inside wall 28, which decreases the diameter of the carotid artery 18. As a result, blood flow is diminished through this area.

The therapeutic interventional procedure comprises implanting an expandable interventional instrument at the interventional procedure site 14, to press the build-up of plaque 26 of the stenosis against the inside wall 28, to increase the diameter of the occluded area 14 of the artery 18, and to help restore sufficient flow of blood to the downstream vessels leading to the brain. The expandable interventional instrument not only helps increase the diameter of the occluded area, but helps prevent restenosis in the area of treatment 14. The interventional instrument is expandable upon deployment thereof at the interventional procedure site 14.

The system 10 of the present invention enables the delivery of a filter device 30 to a location distal to the area of treatment 14, to enable deployment of the filter device 30 at the location distal to the area of treatment 14, and to enable the removal of the filter device 30 from the delivered and deployed position thereof. The filter device 30 filters the blood in the blood vessel 12, so as to pass blood therethrough and capture embolic material 32 which may be released in the blood vessel 12 during the interventional procedure. It is secured to the distal end 22 of the guide wire 16, so as to enable the filter device 30 to be placed within the carotid artery 18 or other blood vessel of the patient and guided into position distal to the area of treatment 14. The filter device 30 includes a proximal portion 34 and a distal portion 36.

Referring to FIGS. 1–10, in embodiments pursuant to the present invention, for example, the system 10 enables compressed low profile movement thereof without a sheath, through the patient's blood vessel 12, to a position distal to the area of treatment 14 for deployment of the filter device 30. The system 10 further enables the release of the compression thereof, for expansion of the filter device 30 against the inside wall 28 of the blood vessel 12 and the sealing off of the inside wall 28, to enable the capture of embolic material 32 which may be released into the blood vessel 12 during the therapeutic interventional procedure.

The system 10 includes the guide wire 16, positionable within the blood vessel 12, and extendable to a position distal to the interventional procedure site 14. The system 10 further includes the filter device 30, which includes a compressing element 38 for compression thereof, to enable the filter device 30 to be compressed in a low profile at the distal end 22 of the guide wire 16, and to be retained in compressed condition, for delivery thereof to the position distal to the interventional procedure site 14, without a sheath extending about the filter device 30. The compressing element 38 is releasable from compressing the filter device 30 at the location distal to the interventional procedure site 14, to enable expansion of the filter device 30 for deployment thereof.

The system 10 further includes an obturator 40, which includes a proximal end 42 and a distal end 44. The obturator 40 extends between the distal portion 36 of the filter device 30 and the tip coil 20. The obturator 40 provides a smooth transition between the distal portion 36 of the filter device 30 and the tip coil 20, so as to enable the distal portion 36 of the filter device 30 to slide smoothly around tortuous anatomy in the blood vessel 12, and to inhibit digging into, scraping, or damaging the inside wall 28 of the blood vessel 12 thereby. The distal portion 36 of the filter device 30 further includes a tube 46, comprised for example of polyimide material, for enabling the obturator 40 to be bonded and assembled thereover.

The filter device 30 further includes a cage 48, which is engageable with the distal end 22 of the guide wire 16, and filter material 50, for filtering embolic material 32, which is secured to the cage 40. The cage 48 includes a proximal portion 52, a medial portion 54, and a distal portion 56. The filter material 50 includes a proximal end 58, a distal end 60, and a plurality of holes 62 therein for filtering embolic material 32. The proximal end 58 of the filter material 50 is secured to the medial portion 54 of the cage 48, and the proximal end 42 of the obturator 40 extends over the distal end 60 of the filter material 50. The proximal portion 52 of the cage 48 includes a channel 64 extending therethrough, and at least one tab 66. The tabs 66 are extendable in the distal direction, and are pre-bent so as to be extendable radially towards the guide wire 16.

The compressing element 38 includes an engageable element 68, engageable with the filter device 30 so as to enable compression of the filter device 30. It further includes an engaging element 70, for engaging the engageable element 68 so as to retain compression of the filter device 30, and for releasing from engagement with the engageable element 68 to enable the release of compression of the filter device 30 for expansion and deployment thereof.

Figure 1:
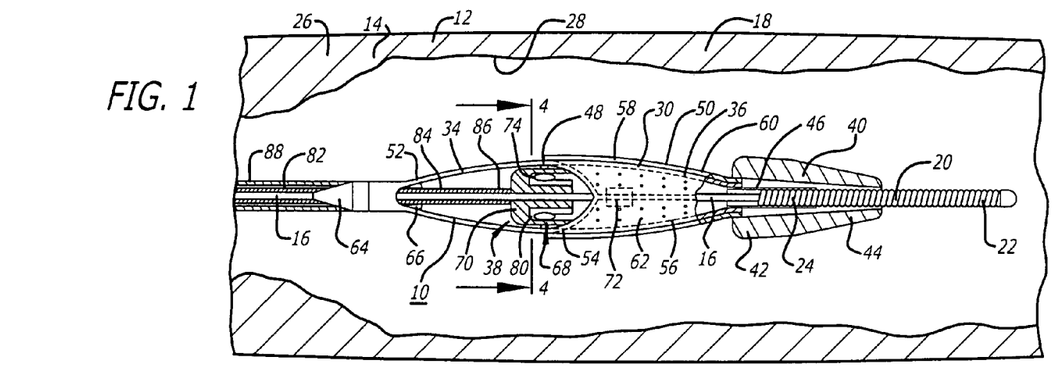
FIG. 1 is an elevational fragmentary partly-sectional view of a first version of a first embodiment of the present invention, disposed within the internal carotid artery of a patient, including a filter device which is compressed and retained in compression by an inner tube extending therein.
Figure 2:
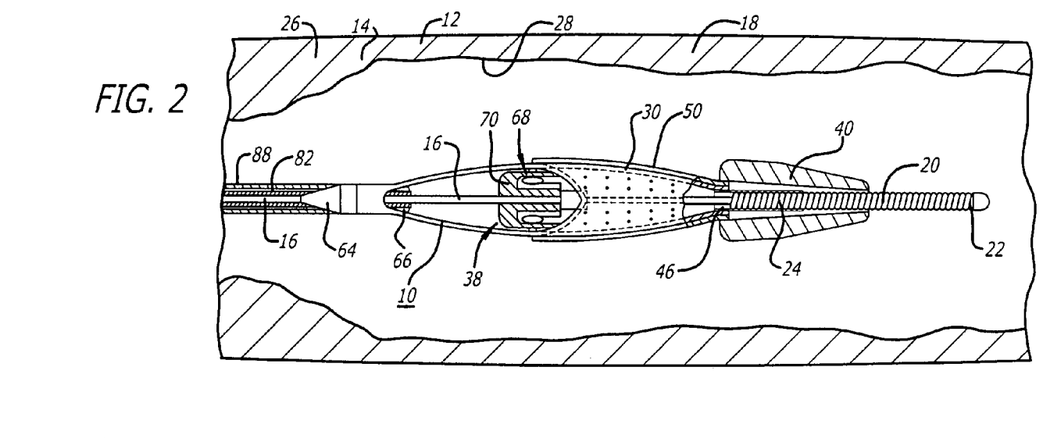
FIG. 2 is a similar view of the first version of the first embodiment shown in FIG. 1, wherein the filter device is compressed and is not retained in compression by the inner tube therein.
Figure 3:
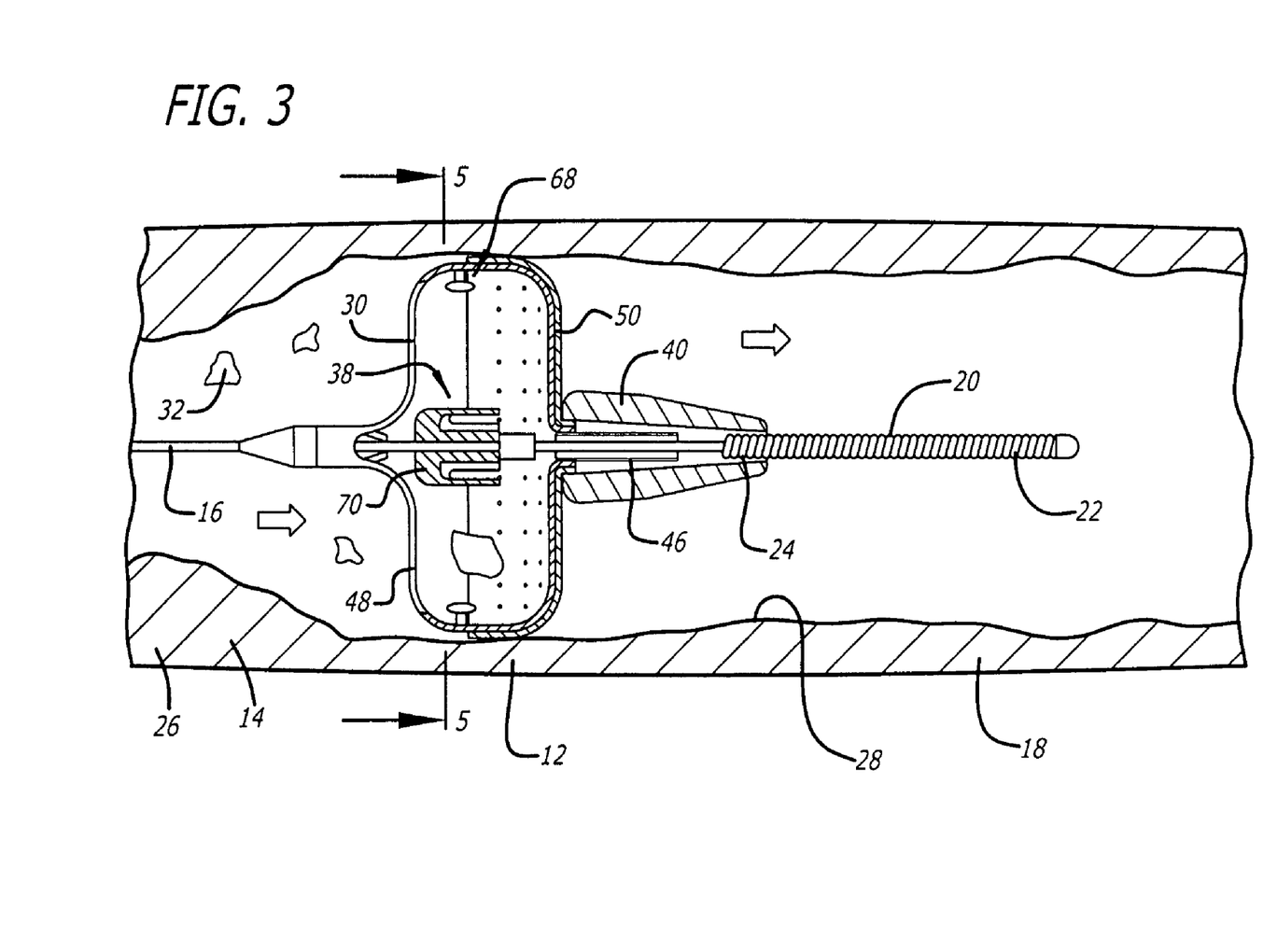
FIG. 3 is a similar view of the first version of the first embodiment shown in FIG. 1, wherein compression of the filter device has been released and the filter device has expanded.
Figure 4:
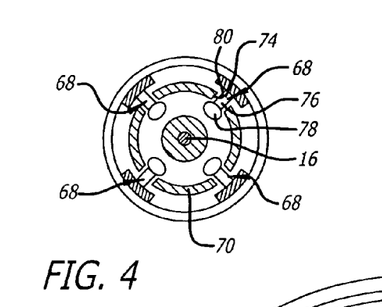
FIG. 4 is a cross-sectional view taken along the line 4—4 of FIG. 1.
Figure 5:
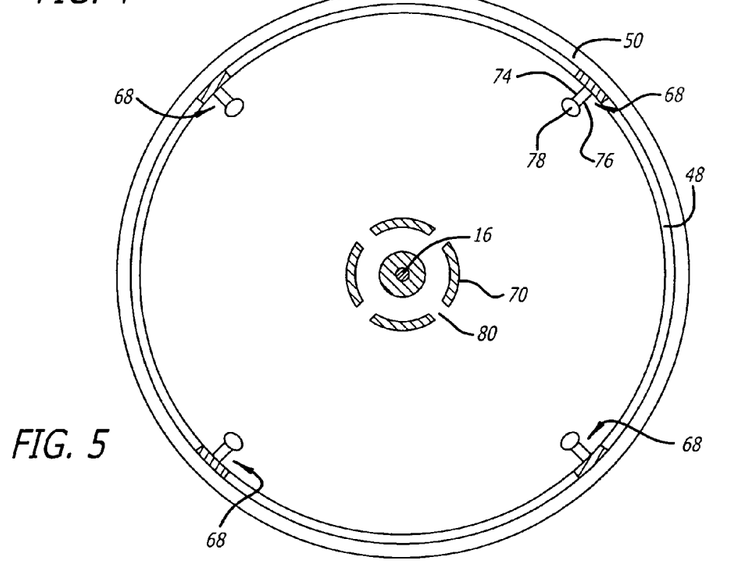
FIG. 5 is a cross-sectional view taken along the line 5—5 of FIG. 3.

In a first version of a first embodiment pursuant to the present invention, as shown in FIGS. 1–5, a stop member 72 is secured to the distal end 22 of the guide wire 16, spaced proximal of the proximal end 24 of the tip coil 20. The stop member 72 may for example comprise a tapered stop which includes a radiopaque marker band thereon, for providing a reference for positioning the filter device 30 in the patient's vasculature 12. The engageable element 68 of the compressing element 38 comprises at least one tab member 74, projecting generally radially inwardly from the outer surface of the cage 48 of the filter device 30. The tab members 74 each include a relatively narrow projecting portion 76, and a relatively enlarged end portion 78. There may for example be four tab members, spaced ninety-degrees apart about the cage 40, as seen in FIGS. 3 and 4. The engaging element 70 for example is generally ring-shaped, and includes at least one slot 80 therein extending and opening in a generally distal direction therein. The tab members 74 of the engageable element 68 are engageable with and releaseable from the slots 80 in the engaging element 70.

The system 10 further includes a delivery enabling element 82, which bears against the compressed filter device 30 for enabling delivery thereof to the position distal to the interventional procedure site 14, without extending about the filter device 30. The delivery enabling element 82 is also able to be withdrawn from bearing against the filter device 30. The delivery enabling element 82 includes an inner tube 84, which is extendable about the guide wire 16, and which includes a distal end 86 which is extendable into the filter device 30, through the channel 64 in the proximal portion 34 thereof, so as to bear against the compressing element 38. The inner tube 84 also pushes the tab members 74 radially outwardly and into engagement therewith upon extending through the channel 64. The delivery enabling element 82 also includes an outer tube 88, extendable about the inner tube 84, which bears against the proximal portion 34 of the filter device 30 for delivery thereof.

Figure 6:
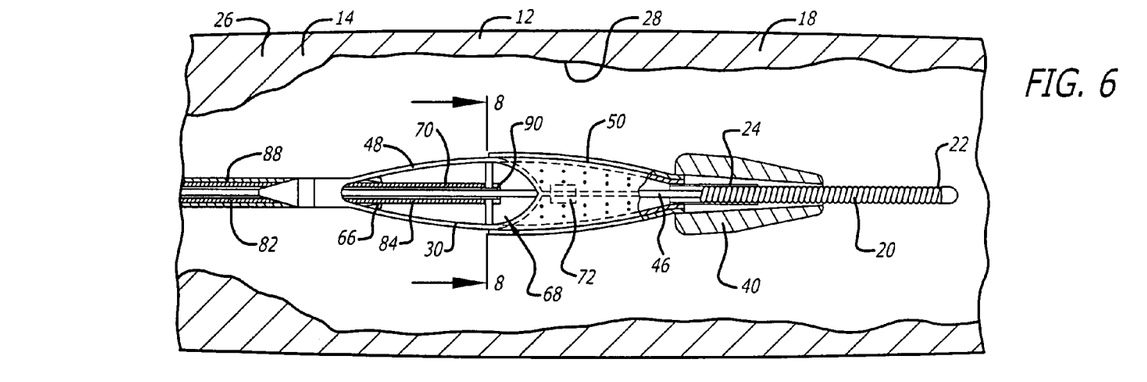
FIG. 6 is an elevational fragmentary partly-sectional view of a second version of the first embodiment of the present invention, disposed within the internal carotid artery of a patient, including a filter device which is compressed and retained in compression by an inner tube extending therein.
Figure 7:
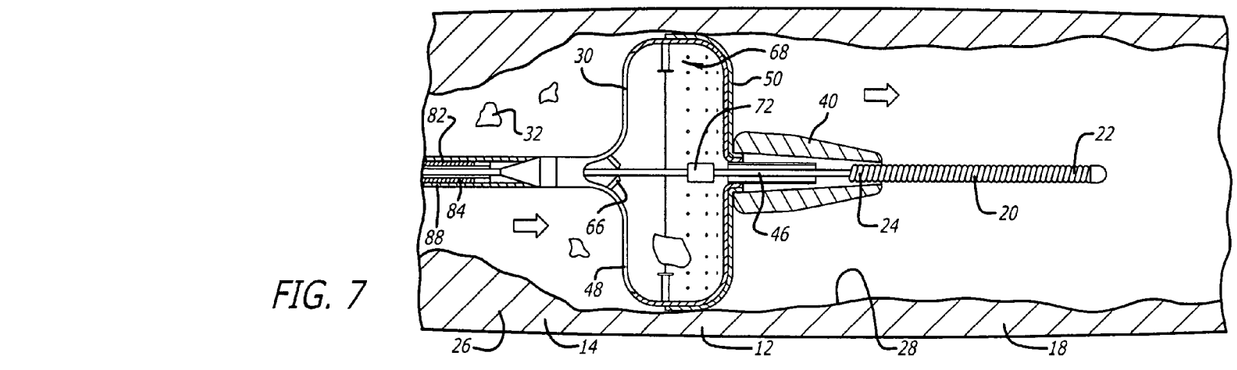
FIG. 7 is a similar view of the second version of the first embodiment in FIG. 6, wherein compression of the filter device has been released and the filter device has expanded.
Figure 8:
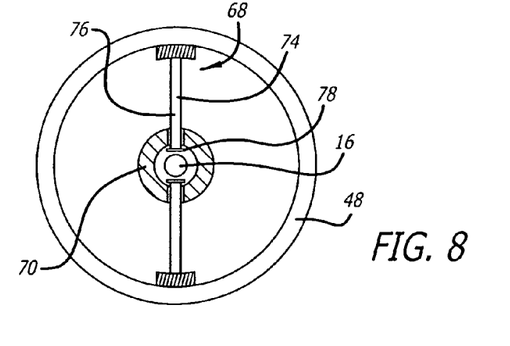
FIG. 8 is a cross-sectional view taken along the line 8—8 of FIG. 6.

As shown in FIGS. 6–8, in a second version of the first embodiment, the inner tube 84 comprises the engaging element 70, and includes at least one slot 90 in the distal end 86 thereof, which opens in the distal direction, for receiving the tab member 74 of the engageable element 68 therein.

Figure 9:
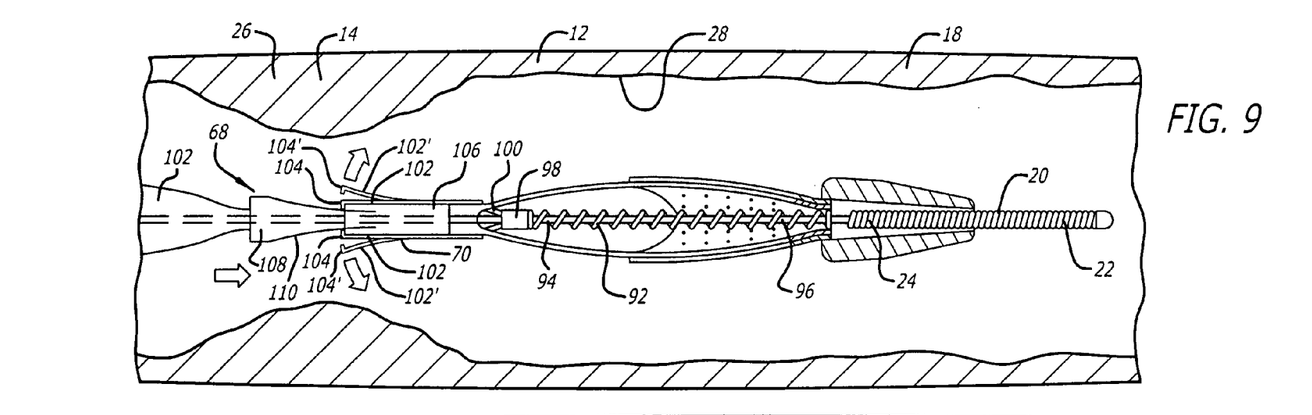
FIG. 9 is an elevational fragmentary partly-sectional view of a second embodiment of the present invention, disposed within the internal carotid artery of a patient, including a filter device which is compressed and retained in compression.
Figure 10:
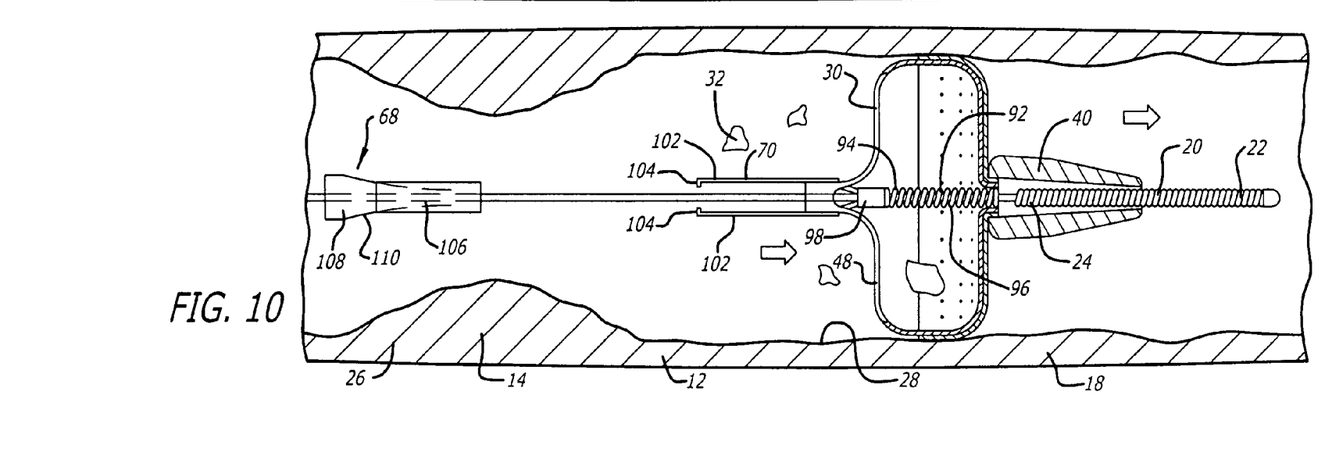
FIG. 10 is a similar view of the second embodiment in FIG. 9, wherein compression of the filter device has been released and the filter device has expanded.

In a second embodiment of the invention, as illustrated in FIGS. 9–10, the filter device 30 further includes a normally-compressed member 92, which is expandable and retained in the expanded condition by the compressing element 38 for compression of the filter device 30. The normally-compressed member 92 is biased to compress upon release of the compressing element 38, to release the compressed filter device 30 for expansion and deployment of the filter device 30. The normally-compressed member 92 includes a proximal end 94 and a distal end 96. The normally-compressed member 92 for example comprises a spring.

The filter device 30 further includes a stop 98 in the proximal portion 34 thereof, and a space 100 between the proximal portion 52 of the cage 40 and the stop 98 into which the tabs 66 are extendable to bear against the stop 98. The proximal end 94 of the spring 92 bears against the stop 98. The filter device 30 also includes an engaging member 102, engageable with the engageable element 68, and releaseable therefrom responsive to engagement of the engaging element 70 with the engageable element 68. The engaging member 102 comprises at least one strut, including a proximal tip portion 104, positionable so as to extend radially inwardly towards the guide wire 16.

The engageable element 68 includes a distal section 106, secured to the guide wire 16, substantially uniform in diameter, which is engageable by the engaging element 70. It further includes a proximal section 108, movable relative to the distal section 106, so as to release the struts 102 of the filter device 30 from engagement with the engageable element 68. The proximal section 108 of the engageable element 68 includes a portion 110, the diameter of which increases in the proximal direction, which guides the struts 102 of the filter device 30 therealong so as to expand radially outwardly upon movement of the proximal section 108 in the distal direction relative to the distal section 106, until the struts 102 release from engagement with the distal portion 106 of the engageable element 68. The engaging element 70 comprises for example a balloon catheter.

Referring to FIGS. 1–10, in a method for the use of the embodiment in accordance with the present invention, for example, the system 10 enables delivery thereof in a low profile through the patient's blood vessel 12 to the location distal to the area of treatment 14 for deployment of the filter device 30, and seals off the inside wall 28 of the blood vessel 12 to enable the capture of embolic material 32. The filter device 30 is compressed by engaging the engaging element 70 with the engageable element 68 of the compressing element 38, so as to engage the compressing element 38 with the filter device 30. The compressed filter device 30 is engaged with the distal end 22 of the guide wire 16. The compressed filter device 30 is then delivered with the guide wire 16 in the low profile, for crossing the stenosis 14, without a sheath extending thereabout, to the location in the patient's vasculature 12 distal to the interventional procedure site 14. The compressing element 38 is then released, by releasing the engaging element 70 from engaging the engageable element 68, so as to enable the filter device 30 to expand and deploy, to capture embolic material 32 which may be released during the interventional procedure.

The delivery enabling element 82, in the first embodiment of the invention as seen in FIGS. 1–6, bears against the compressed filter device 30 for enabling delivery thereof to the position distal to the interventional procedure site 14, without extending about the filter device 30. The delivery enabling element 82 is withdrawn from bearing against the filter device 30, for enabling release of the compressed filter device 30 for expansion and deployment thereof at the position distal to the interventional procedure site 14.

In the first version of the first embodiment of the present invention, as shown in FIGS. 1–5, the slots 80 in the engaging element 70 are engaged with the tab members 74 of the engageable element 68, to compress the filter device 30. An assembly of the compressed filter device 30 is inserted for example over the proximal end of the guide wire 16, extending outside the patient. The compressed filter device 30 is advanced over the proximal end of the guide wire 16 into the patient's body and onto the distal end 22 of the guide wire 16. The distal end 86 of the inner tube 84 of the delivery enabling element 82 is extended through the channel 64 in the proximal portion 34 of the filter device 30 so as to bear against the engaging element 70, to retain the filter device 30 in the compressed condition thereof. The outer tube 88 of the delivery enabling element 82 bears against the proximal portion 34 of the filter device 30 for enabling delivery of the filter device 30 to the location for deployment thereof. Delivery systems may be configured in over the wire or rapid exchange delivery platforms.

Upon reaching the location distal to the interventional procedure site 14, the distal end 86 of the inner tube 84 is pulled in the proximal direction away from its position bearing against the engaging element 70, to a position for example extending slightly distal of the tabs 66, leaving a space between the distal end 86 of the inner tube 84 and the engaging element 70. The guide wire 16 is then pulled in the proximal direction, pulling the stop member 72 into engagement with the engaging element 70. Upon pulling the guide wire 16 further in the proximal direction, the tab members 74 of the engageable element 68 slide out of the slot 80 in the engaging member 70, releasing the tab members 74 from the slots 80 so as to enable expansion and deployment of the filter device 30. Alternatively, for example, a slightly larger tip coil 20 may be used to push the engaging element 70 and deploy the filter device 30.

The slots 90 of the inner tube 84, in the second version of the first embodiment of the invention, as depicted in FIGS. 6–8, engage the tab members 94 of the engageable element 68, to compress the filter device 30, and to retain the filter device 30 in the compressed condition during delivery. The outer tube 88 bears against the proximal portion 34 of the filter device 30 for enabling delivery of the filter device to the deployment location thereof. The distal end 86 of the inner tube 84 is pulled in the proximal direction, away from engagement with the engageable element 68, upon reaching the position distal to the interventional procedure site 14, for releasing the tab members 74 from the slots 80, and the tabs 66 engage the guide wire 16, for enabling expansion and deployment of the filter device 30.

As illustrated in FIGS. 9–10, in the second embodiment of the present invention, an assembly of the filter device 30 and the obturator 40 is inserted for example over the proximal end of the guide wire 16 up to the position where the tabs 66 snap-fit into the space 100 so as to bear against the stop 98. The spring 92 is expanded, and the struts 102 of the filter device 30 engage the distal section 106 of the engageable element 68. The guide wire 16 is then pushed through the patient's vasculature 12, with the filter device 30 in compressed low profile condition, until the distal end 22 of the guide wire 16 reaches the position distal to the interventional procedure site 14. The balloon catheter 70 is then inserted over the guide wire 16 and through the patient's vasculature 14 until it engages the proximal section 108 of the engageable element 68. Upon pushing the balloon catheter 70 further in the distal direction, the proximal section 108 of the engageable element 68 moves distally into the distal section 106 thereof which is secured to the guide wire 16, causing the struts 102 of the filter device 30 to move radially outwardly along the guiding portion 110 of the proximal section 108. Upon sufficient radially-outward movement of the struts 102 along the guiding surface 110 of the proximal section 108 of the engageable element 68, the struts release from engagement with the distal section 106, releasing the filter device 30 from engagement therewith, and enabling the spring 92 to compress, resulting in expansion and deployment of the filter device 30 for capturing embolic material 32.

In accordance with the present invention, the particular embodiments set forth above of the system 10 for filtering embolic material are capable of being positioned in a blood vessel. However, other forms of the system 10 may be utilized with the present invention without departing from the spirit and scope of the invention. For example, the system 10 may be comprised of other forms of material. Additionally, while the system 10 is shown in various shapes in the embodiments herein, it can be formed in any one of a number of different shapes depending upon the construction desired.

Further, the various components may be joined by suitable adhesives such as acrylonitrile based adhesives or cyanoacrylate based adhesives. Heat shrinking or heat bonding may also be employed where appropriate. Plastic-to-plastic or plastic-to-metal joints can be effected by a suitable acrylonitrile or cyanoacrylate adhesive. Variations can be made in the composition of the materials to vary properties as needed. Based on the present disclosure, other adhesives and applications are known to one skilled in the art.

In view of the above, it is apparent that the system and method of the embodiment of the present invention enhances substantially the effectiveness of performing interventional procedures by providing a filter device for filtering embolic material, to be compressed in a low profile for crossing a stenosis without a sheath extending about the filter device, and to be retained in compressed condition thereof, for delivery to a position distal to an interventional procedure site. The system and method further enable release of compression of the filter device at the location distal to the area of treatment of the stenosis, enabling the filter device to expand and deploy so as to capture embolic material.

While the present invention has been described in connection with the specific embodiments identified herein, it will be apparent to those skilled in the art that many alternatives, modifications and variations are possible in light of the above description. Accordingly, the invention is intended to embrace all such alternatives, modifications and variations as may fall within the spirit and scope of the invention disclosed herein.

What is claimed is:

1. A system for enabling the capture of embolic material which may be released into a blood vessel during a therapeutic interventional procedure at a site of a stenosis, comprising:
    a guide wire, including a distal end, adapted to be positioned within the blood vessel and to extend to a position distal to an interventional procedure site and a proximal end, adapted to remain outside of the blood vessel during the therapeutic procedure; and
    a filter device having an interior and an exterior, adapted to be positioned and deployed at a location in the patient's vasculature distal to the interventional procedure site, and to capture embolic material which may be released into the blood in the blood vessel during the interventional procedure, including a compressing element located in the interior of the filter device, for compressing the filter device so as to enable the filter device to be inserted over the guide wire, to the position distal to the interventional procedure site, in a low profile for crossing the stenosis, and without a sheath extending about the filter device, adapted to enable release thereof so as to enable expansion of the filter device for deployment thereof.

2. The system of claim 1, wherein the compressing element comprises an engageable element in the filter device, adapted to enable engagement therewith so as to compress the filter device, and an engaging element, adapted to enable engagement thereof with the engageable element so as to compress the filter device, and to enable release thereof from engagement with the engageable element for enabling expansion of the filter device and deployment thereof.

3. The system of claim 1, further comprising a delivery enabling element, adapted to bear against the compressed filter device for enabling delivery thereof to the position distal to the interventional procedure site, without extending about the filter device, and adapted to be withdrawn from bearing against the filter device for enabling release of the compressed filter device for expansion and deployment thereof at the position distal to the interventional procedure site.

4. The system of claim 1, wherein the guide wire includes a stop member, adapted to be secured to the distal end of the guide wire and within the filter device, for enabling the compressing element to bear against the stop member for enabling release of the compressing element for expansion and deployment of the filter device.

5. The system of claim 2, wherein the engageable element comprises at least one tab member, projecting from the inner surface of the filter device and projecting inwardly therefrom.

6. The system of claim 2, wherein the filter device includes a normally-compressed member, adapted to be expanded, and to be retained in expanded condition by the compressing element for compression of the filter device, and wherein the normally-compressed member is biased to compress upon release of the compressing element, to release the compressed filter device for expansion and deployment of the filter device.

7. The system of claim 3, wherein the delivery enabling element includes an inner tube, adapted to extend about the guide wire, and including a distal end which is adapted to be extendable into the filter device so as to bear against the compressing element, and an outer tube, extendable about the inner tube, adapted to bear against the proximal end of the filter device for delivery thereof.

8. The system of claim 5, wherein the engageable element comprises a restraining ring, including at least one slot therein opening in the distal direction for receiving the tab member therein.

9. The system of claim 5, wherein the engaging element comprises an inner tube, adapted to extend about the guide wire, and including a distal end which is adapted to be extendable into the filter device, and which includes at least one slot therein opening in the distal direction for receiving the tab member therein.

10. The system of claim 5, wherein the at least one tab member comprises a plurality of tab members, located at positions equally spaced apart in the filter device.

11. The system of claim 6, wherein the filter device includes an engaging member, adapted to engage the engageable element, and to be releaseable therefrom responsive to engagement of the engaging element which the engageable element.

12. The system of claim 6, wherein the normally-compressed member comprises a spring.

13. The system of claim 7, wherein the filter device includes a proximal end, which includes a proximal bushing, having a channel therein for enabling the inner tube to extend therethrough.

14. The system of claim 10, wherein the engaging element includes a plurality of slots therein, opening in the distal direction for receiving the plurality of tab members therein.

15. The system of claim 11, wherein the engageable element includes a distal section, adapted to be secured to the guide wire, and a proximal section, adapted to be engaged by the engaging member, and to be movable relative to the distal section so as to release the engaging member of the filter device from engagement with the engageable element.

16. The system of claim 11, wherein the engaging member comprises at least one strut, which includes a proximal tip portion adapted to extend radially inwardly towards the guide wire.

17. The system of claim 11, wherein the filter device includes a proximal portion, and the engaging member is adapted to extend in the proximal direction from the proximal portion of the filter device.

18. The system of claim 13, wherein the proximal end of the filter device further includes at least one tab, adapted to extend in the distal direction and to be pre-bent so as to be biased to extend radially towards the guide wire, and to enable the inner tube to extend therethrough and to push the tab radially outwardly upon extending therethrough.

19. The system of claim 15, wherein the proximal section of the engageable element includes a portion extendable in the distal direction, adapted to guide the engaging member of the filter device therealong upon movement of the proximal section relative to the distal section until the engaging member releases from engagement with the engageable element.

20. The system of claim 15, wherein the engaging element comprises a balloon catheter.

21. A method of enabling the capture of embolic material which may be released into a blood vessel during a therapeutic interventional procedure at a site of a stenosis, in a system which comprises a guide wire, including a distal end, adapted to be positioned within the blood vessel and to extend to a position distal to an interventional procedure site and a proximal end, adapted to remain outside of the blood vessel during the therapeutic procedure, and a filter device having an interior and an exterior, adapted to be positioned and deployed at a location in the patient's vasculature distal to the interventional procedure site, and to capture embolic material which may be released into the blood in the blood vessel during the interventional procedure, including a compressing element located in the interior of the filter device, for compressing the filter device so as to enable the filter device to be inserted over the guide wire, to the position distal to the interventional procedure site, in a low profile for crossing the stenosis, and without a sheath extending about the filter device, adapted to enable release thereof so as to enable expansion of the filter device for deployment thereof, wherein the method comprises:

compressing the filter device, comprising engaging the compressing element with the filter device;

engaging the compressed filter device for movement along the guide wire;

delivering the compressed filter device along the guide wire in a low profile for crossing the stenosis and without a sheath extending thereabout, to the location in the patient's vasculature distal to the interventional procedure site while the proximal end of the guide wire remains outside of the blood vessel; and releasing the compressing element so as to release the filter device from compression thereof, for expansion and deployment of the filter device.

22. The method of claim 21, further comprising a delivery element, adapted to bear against the compressed filter device for enabling delivery thereof to the position distal to the interventional procedure site, without extending about the filter device, and adapted to be withdrawn from bearing against the filter device for enabling release of the compressed filter device for expansion and deployment thereof at the position distal to the interventional procedure site, and wherein delivering comprises the delivery element bearing against the filter device, and releasing comprises withdrawing the delivering element from bearing against the filter device.

23. A method of enabling the capture of embolic material which may be released into a blood vessel during a therapeutic interventional procedure at a site of a stenosis, in a system which comprises a guide wire, including a distal end, adapted to be positioned within the blood vessel and to extend to a position distal to an interventional procedure site and a proximal end, adapted to remain outside of the blood vessel during the therapeutic procedure, and a filter device having an interior and an exterior, adapted to be positioned and deployed at a location in the patient's vasculature distal to the interventional procedure site, and to capture embolic material which may be released into the blood in the blood vessel during the interventional procedure, including a compressing element located in the interior of the filter device, for compressing the filter device so as to enable the filter device to be inserted over the guide wire, to the position distal to the interventional procedure site, in a low profile for crossing the stenosis, and without a sheath extending about the filter device, adapted to enable release thereof so as to enable expansion of the filter device for deployment thereof, wherein the method comprises:
 compressing the filter device, comprising engaging the compressing element with the filter device;
 engaging the compressed filter device with the distal end of the guide wire;
 delivering the compressed filter device engaged with the guide wire in a low profile for crossing the stenosis and without a sheath extending thereabout, to the location in the patient's vasculature distal to the interventional procedure site while the proximal end of the guide wire remains outside of the blood vessel; and
 releasing the compressing element so as to release the filter device from compression thereof, for expansion and deployment of the filter device, wherein the compressing element comprises an engageable element in the filter device, adapted to enable engagement therewith so as to compress the filter device, and an engaging element, adapted to enable engagement thereof with the engageable element so as to compress the filter device, and to enable release thereof from engagement with the engageable element for enabling expansion of the filter device and deployment thereof, wherein compressing comprises engaging the engageable element with the filter device, and releasing comprises releasing the engaging element from engagement with the engageable element.

24. The method of claim 23, wherein the engageable element comprises at least one tab member, projecting from the outer surface of the filter device inwardly therefrom, and wherein compressing further comprises engaging the engaging element with the tab member of the engageable element.

25. The method of claim 23, wherein the filter device includes a normally-compressed member, adapted to be expanded, and to be retained in expanded condition by the compressing element for compression of the filter device, and wherein the normally-compressed member is biased to compress upon release of the compressing element, to release the compressed filter device for expansion and deployment of the filter device, and wherein compressing comprises expanding the normally-compressed member and retaining the normally-compressed member in expanded condition, and releasing comprises releasing the normally-compressed member for enabling compression thereof.

26. The method of claim 24, wherein the engaging element comprises an inner tube, adapted to extend about the guide wire, and including a distal end which is adapted to be extendable into the filter device, and which includes at least one slot therein opening n the distal direction for receiving the tab member therein and wherein engaging further comprises engaging the slot in the inner tube with the tab member.

27. A method of enabling the capture of embolic material which may be released into a blood vessel during a therapeutic interventional procedure at a site of a stenosis, in a system which comprises a guide wire, including a distal end, adapted to be positioned within the blood vessel and to extend to a position distal to an interventional procedure site and a proximal end, adapted to remain outside of the blood vessel during the therapeutic procedure, and a filter device having an interior and an exterior, adapted to be positioned and deployed at a location in the patient's vasculature distal to the interventional procedure site, and to capture embolic material which may be released into the blood in the blood vessel during the interventional procedure, including a compressing element located in the interior of the filter device, for compressing the filter device so as to enable the filter device to be inserted over the guide wire, to the position distal to the interventional procedure site, in a low profile for crossing the stenosis, and without a sheath extending about the filter device, adapted to enable release thereof so as to enable expansion of the filter device for deployment thereof, wherein the method comprises:
 compressing the filter device, comprising engaging the compressing element with the filter device;
 engaging the compressed filter device with the distal end of the guide wire;
 delivering the compressed filter device engaged with the guide wire in a low profile for crossing the stenosis and without a sheath extending thereabout, to the location in the patient's vasculature distal to the interventional procedure site while the proximal end of the guide wire remains outside of the blood vessel; and
 releasing the compressing element so as to release the filter device from compression thereof, for expansion and deployment of the filter device, wherein the guide wire includes a stop member, adapted to be secured to the distal end of the guide wire, and within the filter device, for enabling the compressing element to bear against the stop member for enabling release of the compressing element for expansion and deployment of the filter device, and wherein releasing comprises bearing the compressing element against the stop member.

28. A system for capturing embolic material in a body vessel, comprising:
 a guide wire;
 a stop member disposed on the guide wire;
 a filter device slidably disposed on the guide wire, the filter device having an interior and an exterior and including a self-expanding cage and a filter element attached to the self-expanding cage, the self-expanding cage being movable between a compressed delivery position and a deployed position; and
 a compressing element located in the interior of the filter device for compressing and maintaining the self-expanding cage in the compressed delivery position, the compressing element being removably connected to the self-expanding cage and adapted to disengage from the self-expanding cage by movement between the stop member against the compressing member which allows the self-expanding cage to move into the deployed position.

29. The system of claim 28, further including a delivery enabling element adapted to move the filter device along the guide wire.

30. The system of claim 29, wherein the delivery enabling element is adapted to achieve movement of the compressing element against the stop member to disengage the compressing element from its connection with the self-expanding cage.

31. The system of claim 28, further including a locking mechanism for locking the filter device to the guide wire.

32. The system of claim 31, wherein the locking mechanism has a locked position and an unlocked position.

33. The system of claim 32, further including a component on the delivery enabling element which maintains the locking mechanism in the unlocked position.

34. The system of claim 33, wherein the component on the delivery enabling element that maintains the locking mechanism in the unlocked position abuts against the locking mechanism to maintain the unlocked position and the locking mechanism is adapted to move to the locked position when the abutting relationship between the component and the locking mechanism is removed.

35. The system of claim 31, wherein the locking mechanism is a tab which moves between a first unlocked position and a second locked position in which the tab contacts the guide wire to lock the filter element to the guide wire.

* * * * *

UNITED STATES PATENT AND TRADEMARK OFFICE
CERTIFICATE OF CORRECTION

| | | |
|---|---|---|
| PATENT NO. | : 7,018,393 B1 | Page 1 of 1 |
| APPLICATION NO. | : 09/945152 | |
| DATED | : March 28, 2006 | |
| INVENTOR(S) | : William J. Boyle et al. | |

It is certified that error appears in the above-identified patent and that said Letters Patent is hereby corrected as shown below:

Column 1,
Line 17, delete "110".

Column 3,
Line 41, delete "recover" and insert --recovery--.

Column 11,
Line 56, delete "engaging element which" and insert --engaging element with--.

Column 14,
Line 10, delete "opening n" and insert --opening in--.

Signed and Sealed this

Thirtieth Day of January, 2007

JON W. DUDAS
*Director of the United States Patent and Trademark Office*